United States Patent [19]

Yoshioka et al.

[11] 4,183,855
[45] Jan. 15, 1980

[54] OXAZOLINOAZETIDINYLBUTYRIC ACID DERIVATIVES

[75] Inventors: Mitsuru Yoshioka; Shoichiro Uyeo, both of Toyonaka; Teruji Tsuji, Takatsuki; Yoshio Hamashima, Kyoto; Ikuo Kikkawa, Takarazuka; Wataru Nagata, Nishinomiya, all of Japan

[73] Assignee: Shionogi & Co., Ltd., Osaka, Japan

[21] Appl. No.: 881,054

[22] Filed: Feb. 24, 1978

[30] Foreign Application Priority Data

Feb. 25, 1977 [JP] Japan ................................. 52-20468

[51] Int. Cl.² .......................................... C07D 498/04
[52] U.S. Cl. .................................. 260/307 F; 544/90; 544/92; 260/245.3; 260/239 A
[58] Field of Search ...................................... 260/307 F

[56] References Cited

PUBLICATIONS

Stoodley et al.—C.A. 80, 133329n (1974).
Stoodley et al.—C.A. 83, 58697 (1975).
Asinger, F.—"Mono-Olefins, Chemistry and Technology"—Pergamon Press (1968)—pp. 714, 756, 759–760.

Primary Examiner—Mark L. Berch
Attorney, Agent, or Firm—Wenderoth, Lind & Ponack

[57] ABSTRACT

Intermediates (I) for preparing a potent antibacterial, 1-oxadethiacephalosporin, are shown by the following formula

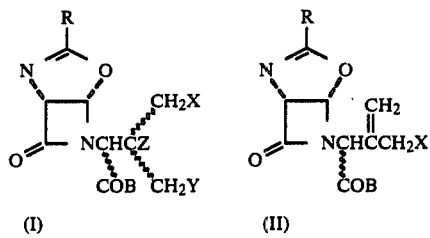

(wherein
R is a group of acyl-minus-carbonyl derived from a carboxylic or carbonic acid;
COB is carboxy or protected carboxy;
X is hydrogen or a nucleophilic group;
Y is a nucleophilic group; and
Z is a leaving group)

and prepared from the corresponding exomethylene compound (II) by addition of a compound of formula: Y-Z (in which Y and Z are as defined above).

1 Claim, No Drawings

OXAZOLINOAZETIDINYLBUTYRIC ACID DERIVATIVES

This invention relates to new intermediates for preparing a potent antibacterial, 1-dethia-1-oxacephalosporin, and to the synthesis thereof. More specifically, it relates to oxazolinoazetidinylbutyric acid derivatives of formula I given later.

I. INTRODUCTION

1-Dethia-1-oxacephalosporins are modern antibacterials of broad antibacterial spectra. The present inventors have searched for an effective synthesis to find a route in which Compounds I given later are key-intermediates.

Said 1-dethia-1-oxacephalosporins are represented by the following formula:

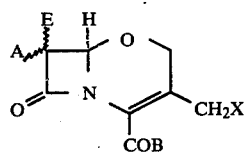

(wherein
   A is amino or substituted amino;
   E is hydrogen or methoxy;
   X is hydrogen or a nucleophilic group; and
   COB is carboxy or protected carboxy),
in which those (where A=acylamino, E=methoxy, X=heteroaromatic thio, and COB=COOH) or their salts are especially useful (Christensen: J. Am. Chem. Soc., 96, 7582 (1974)).

(Prior Synthesis)

The 1-dethia-1-oxacephalosporins have been prepared by several synthetic routes given below, but the formation of undesired isomers at position 4 of the azetidinone ring is inevitable and yields of the desired intermediates do not usually exceed 50%.
(Japanese Patent Publication (Unexamined) 51-149,295)

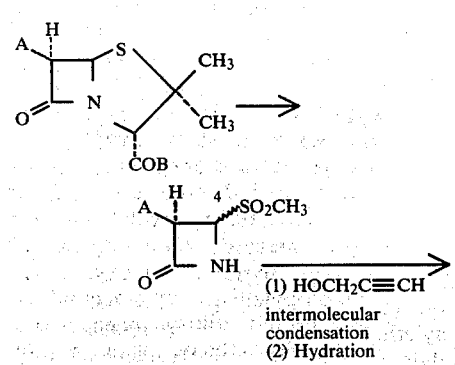

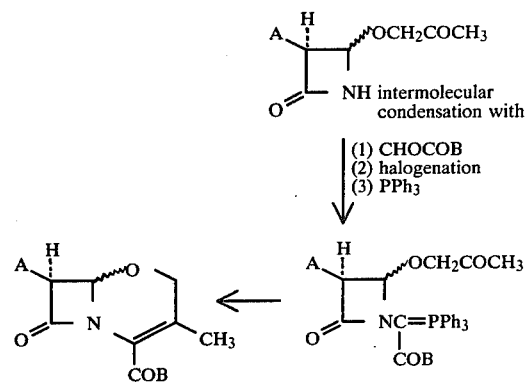

(Japanese Patent Publication (Unexamined) 51-41,385)
Canadian Journal of Chemistry 52 3996 (1974)

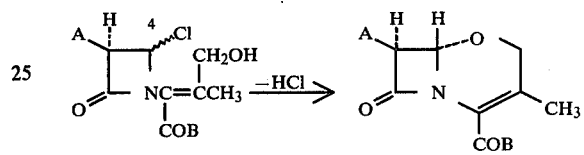

(Japanese Patent Publication (Unexamined) 49-133,594)

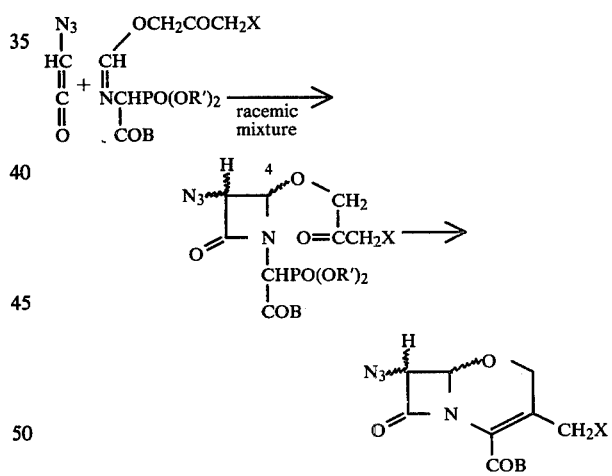

(wherein
   A, COB, and X are as defined above;
   Ph is phenyl; and
   R' is aryl or alkyl)

(New Synthetic Route)

Now the following synthesis is found to work well as a result of stereospecific introduction of the oxygen function at position 4 of the azetidinone ring, using all carbon skeleton of the penicillin nucleus, and shorter reaction steps in an easier and high yield handling for preparing the final products.

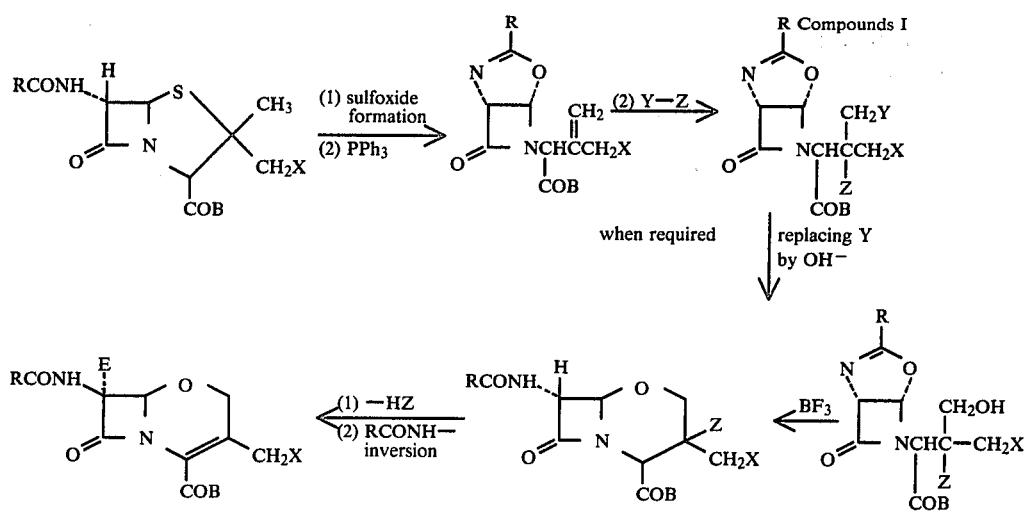

(wherein R, COB, X, Y, Z and E are as defined above)

The compounds I are key-intermediates in this industrially available synthetic route.

II. COMPOUNDS

Thus, the compounds of this invention are shown by the following formula:

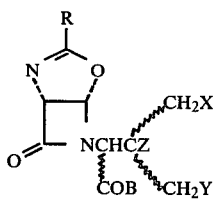

(I)

(wherein
R is a monovalent group of acyl-minus-carbonyl derived from carbonic or carboxylic acid;
COB is carboxy or protected carboxy;
X is hydrogen or a nucleophilic group;
Y is a nucleophilic group; and
Z is a leaving group).

Each symbol of R, COB, X, Y and Z is explained below:

1. (R group)

R is a monovalent group resulting from the elimination of the carbonyl function of an acyl moiety derived from a carboxylic or carbonic acid, or in other words, a group having the constitution acyl less carbonyl derived from a carboxylic or carbonic acyl represented by RCO—, and preferably contains from 1 to 15 carbon atoms. Typical examples of R include hydrogen, 1–6C alkyl (e.g. methyl, ethyl, propyl, isopropyl, butyl, t-butyl), cyclopentylmethyl, 7–15C aralkyl (e.g. benzyl, phenethyl, diphenylmethyl), 7–9C aryloxyalkyl (e.g. phenoxymethyl, phenoxyethyl, phenoxypropyl), 6–10C aryl (e.g. phenyl, naphthyl), 1–6C, alkoxy (e.g. methoxy, ethoxy, propoxy, cyclopropylmethoxy, cyclohexyloxy, 7–15C aralkoxy (e.g. benzyloxy, phenethyloxy), 6–10C aryloxy (e.g. phenoxy, naphthyloxy), carbamoyl, 2–7C carbalkoxy, and the like monovalent groups. These can further be substituted with another group e.g. hydroxy, 1–6C acyloxy (e.g. formyloxy, acetoxy, propionyloxy, pentanoyloxy), 1–3C alkoxy (e.g. methoxy, ethoxy, propoxy), 7–9C aralkoxy (e.g. benzyloxy, tolylmethoxy, xylylmethoxy, anisyloxy, nitrobenzyloxy, halobenzyloxy), 6–8C aryloxy (e.g. phenoxy, xylyloxy), oxo, amino, 1–3C alkylamino (e.g. methylamino, dimethylamino), 1–5C acylamino (e.g. acetamido, propionamido, valeramido), nitro, 1–3C alkyl (e.g. methyl, ethyl, propyl), 6–10C aryl (e.g. phenyl, xylyl), carboxy, protected carboxy, cyano, halo, or like substituents, or can optionally be unsaturated. The aryl part of said groups can also be five or six membered carbocyclic or heterocyclic aromatic groups including phenyl, naphthyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, quinolyl, isoquinolinyl, and benzothiazolyl.

Specific examples of R group include hydrogen, methyl, ethyl, propyl, isopropyl, butyl, methoxymethyl, carbethoxy, trichloroethoxycarbonyl, acetoxyethyl, chloroethyl, allyl, benzyl, nitrobenzyl, chlorobenzyl, aminobenzyl, acetamidobenzyl, bromobenzyl, methoxybenzyl, ethoxybenzyl, methylenedioxybenzyl, trimethoxybenzyl, dichlorobenzyl, hydroxybenzyl, phenethyl, chlorophenethyl, methylphenethyl, nitrophenethyl, methoxyphenethyl, diphenylmethyl, α-chlorobenzyl, α-bromobenzyl, benzyloxybenzyl, anisyloxybenzyl, α-protected carboxybenzyl, α-protected carboxy-p-anisyloxybenzyl, α-protected carboxy-p-diphenylmethoxybenzyl, α-protected carboxyacetyloxybenzyl, furylmethyl, thienylmethyl, oxazolylmethyl, isoxazolylmethyl, thiazolylmethyl, thiadiazolylmethyl, pyrazolylmethyl, tetrazolylmethyl, α-carbalkoxy-α-thienylmethyl, carbomethoxy, carbethoxy, benzyloxycarbonyl, carbamoyl, phenoxymethyl, phenoxyethyl, phenoxypropyl, phenoxybutyl, isoxazolyloxymethyl, phenyl, tolyl, xylyl, hydroxyphenyl, acetoxyphenyl, methoxyphenyl, t-butyloxyphenyl, nitrophenyl, cyanophenyl, carbethoxyphenyl, aminophenyl, acetamidophenyl, methylaminophenyl, chlorophenyl, bromophenyl, thienyl, furyl, pyrrolyl, oxazolyl, oxadiazolyl, oxatriazolyl, thiazolyl, thiadiazolyl, pyrazolyl, triazolyl, tetrazolyl, pyridyl, t-butoxy, cyclopropylmethoxy, cyclopropylethoxy, cyclopentyloxy, methanesulfonylethoxy, trichloroethoxy, phenacyloxy, benzyloxy, xylyloxy, diphenylmethoxy, phenoxy, tolyloxy, naphthyloxy, pentachlorophenoxy, nitrobenzyloxy, pyridyloxy, and benzothiazolyloxy.

The group RCO— can be removed or introduced when desired, and the structure thereof can be varied widely or easily exchangeable in whole course of the synthesis. The structure of choice can be selected by considering stability during the reaction and work-up.

2. (COB group)

The protected carboxy for COB, preferably containing up to 20 carbon atoms, is conventional one in the field of β-lactam antibiotics and is stable under the reaction conditions of this invention. Preferably, said carboxy for COB is protected in the forms of, for example, ester [e.g. 1–5C alkyl (e.g. methyl, ethyl, t-butyl), cyclopropylmethyl, 7–20C aralkyl (e.g. benzyl, phenethyl, diphenylmethyl, trityl), 6–10C aryl (e.g. phenyl, indanyl, naphthyl), or 3–10C organometallic (e.g. trimethylsilyl, ethoxydimethylsilyl, trimethylstannyl) esters], 1–8C amide (e.g. dimethylamide, dibutylamide, diisopropylhydrazide), alkali metal salt (e.g. lithium, sodium, or potassium salt), alkaline earth metal salt (e.g. magnesium, calcium, barium salt), aluminum salt, acid anhydride, or acid halide. The protecting part B may have further substituent such as halo, hydroxy, 1–5C acyloxy (e.g. formyloxy, acetoxy, propionyloxy, butyryloxy, isobutyryloxy, pentanoyloxy), oxo, 1–5C acylamino (e.g. acetamido, propionamido, valeramido), nitro, 1–3C alkyl (e.g. methyl, ethyl, propyl, isopropyl), carboxy, 2–6C carbalkoxy (e.g. carbomethoxy, carbethoxy, propoxycarbonyl, butoxycarbonyl), 1–5C acyl (e.g. acetyl, propionyl, butyryl, pentanoyl), or cyano.

Specific examples of COB group include optionally substituted alkyl esters e.g. methyl, ethyl, isopropyl, propyl, butyl, t-butyl, pentyl, cyclopropylmethyl, cyclopropylethyl, cyclopropylbutyl, monohydroxy-t-butyl, trichloroethyl, chloromethyl, cyanomethyl, methanesulfonylethyl, acetylmethyl, diacetylmethyl, acetoxymethyl, propionyloxymethyl, benzoyloxymethyl, methoxymethyl, methoxyethoxymethyl, carbethoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, and allylesters; aralkyl esters e.g. benzyl, phenethyl, tolylmethyl, dimethylbenzyl, nitrobenzyl, halobenzyl, methoxybenzyl, phthalidyl, anthrylmethyl, p-hydroxy-3,5-di-t-butylbenzyl, diphenylmethyl, methoxydiphenylmethyl, trityl, phenacyl, chlorophenacyl, bromophenacyl, nitrophenacyl, and methylphenacyl esters; armatic esters e.g. phenyl, naphthyl, tolyl, dimethylphenyl, nitrophenyl, methanesulfonylphenyl, chlorophenyl, pentachlorophenyl, indanyl, and pyridyl esters; and organometallic esters e.g. trimethylsilyl, dimthylmethoxysilyl, methylenedioxymethylsilyl, trimethylstannyl esters; alkali metal or alkaline earth metal salts e.g. sodium, potassium, magnesium, calcium, aluminum, acyloxycalcium, and barium salts, organic base salts e.g. triethylammonium and dicyclohexylammonium salt; mixed anhydride with acetic acid or 1–5C alkyl half carboxylate; and in some cases, chloride and bromide.

3. (X group)

The nucleophilic group for X includes every possible group introduced in place of the acetoxy attached to the methylene at position 3 of cephalosporanic acid derivatives, and containing preferably up to 15 carbon atoms.

Typical examples of X include hydrogen, halo (e.g. chloro, bromo, iodo), hydroxy, up to 5C acyloxy (e.g. nitroxy, sulfurous acyloxy, formyloxy, acetoxy, propionyloxy, butyryloxy, pentanoyloxy, trifluoroacetoxy, trichloroacetoxy, β-hydroxypropionyloxy, haloacetyloxy, β-hydroxypropionyloxy, benzoyloxy, nicotinoyloxy, carbamoyloxy, methoxycarbonyloxy, aminopropionyloxy, sulfenyloxy, sulfonyloxy, sulfinyloxy), 1–6C alkoxy (e.g. methoxy, ethoxy, propoxy, butoxy, hexyloxy), cyclohexyloxy, cyclopropylmethoxy, tetrahydropyranyloxy, thiocarbamoylthio, 1–5C alkylthio (e.g. methylthio, ethylthio, pentylthio), 6–10C arylthio (e.g. phenylthio, tolylthio, nitroophenylthio, naphthylthio, thienylthio, methyltetrazolylthio, methanesulfonylethyltetrazolylthio, carboxyethyltetrazolylthio, protected carboxyethyltetrazolylthio, protected sulfonylethyltetrazolylthio, methylaminoethyltetrazolylthio, dimethylaminoethyltetrazolylthio, dimethylaminoethyltetrazolylthio, morpholinoethyltetrazolylthio, thiadiazolylthio, methylthiadiazolylthio, carboxymethylthiadiazolylthio, protected carboxymethylthiadiazolylthio, protected hydroxymethylthiadiazolylthio, aminomethylthiadiazolylthio, methylaminomethylthiadiazolylthio, triazolylthio, 1–3C alkyl-5-hydroxy-6-oxo-1,6-dihydro-1,3,4-triazin-2-ylthio), 1–6C alkylsulfinyl (e.g. methylsulfinyl, ethylsulfinyl, phenylsulfinyl, 1-methyl-5-tetrazolylsulfinyl), and the like nucleophilic groups.

Preferably X is a leaving group for a successive substitution e.g. halo, haloalkanoyloxy, or sulfonyloxy cited above. Alternatively, it is an aimed group bound to the final antibacterial, being a function linked to the methylene at position 3 of 1-oxadethiacephem nucleus e.g. said lower alkanoyloxy, carbamoyloxy, or heteroaromatic thio (especially, triazolylthio, thiadiazolylthio, or tetrazolylthio optionally substituted by 1–2C alkyl).

4. (Y group)

Y is hydrogen or a nucleophilic group. Said nucleophilic group includes those cited above for the X group. After simple or multiple reaction steps, Y can be replaced by hydroxy or a close equivalent, which then replaces the oxazoline oxygen at position 4 of azetidinone ring to form the 1-dethia-1-oxacepham derivatives.

Representative Y is hydroxy, halo (e.g. chlorine, bromine, iodine), acyloxy (e.g. formyloxy, acetoxy, trifluoroacetoxy, methanesulfonyloxy, toluene-p-sulfonyloxy, benzoyloxy, nicotinoyloxy, carbamoyloxy, methoxybarbonyloxy), alkoxy (e.g. t-butoxy, tetrahydropyranyloxy, methoxymethoxy, acetoxymethyl, chloromethoxy), aralkoxy (e.g. benzyloxy, p-methoxybenzyloxy, p-nitrobenzyloxy, trityloxy), thiocarbamoylthio, alkylthio (e.g. methylthio, ethylthio, butylthio, isobutylthio), phenylthio, substituted phenylthio, heteroaromatic thio, and other groups cited for X. Said halogen, acyloxy, alkoxy, or aralkoxy may be subjected to hydrolysis or hydrogenolysis, if required after converting into other nucleophile, to give the objective hydroxy. Said thio groups may be oxidized to give the corresponding sulfoxide, rearranged to sulfenyloxy, and then hydrolyzed to form the objective hydroxy. Said halo groups may be treated with alkali metal nitrate to give nitroxy group which is brought to contact with wet silica gel to give the desired hydroxy. Chloro and bromo can be replaced by iodo with e.g. sodium iodide. Other conventional replacements and reactions are applicable for changing the group Y to give hydroxy. Thus, Y has a wide scope of structure to be selected desiring the hydroxy group.

5. (Leaving group Z)

Leaving group Z includes not only generally accepted ones, but, in this case, includes groups which are readily convertible to leaving groups.

Representative Z includes hydroxy, acyloxy, alkoxy, arylthio, alkylthio, alkylsulfinyl, arylsulfinyl, alkylsulfonyl, alkylsulfonyloxy, arylsulfonyloxy, arylsulfonyloxy, halo, and like leaving groups as explained for X.

Y and Z taken together may form epoxy, alkylenedioxy, epithio, or the like groups.

More preferable compounds have the following figures in the general formula I:

R is selected from the group consisting of phenyl, benzyl, phenoxymethyl, methyl, and hydrogen;

X and Y each is selected from the group consisting of hydroxy, $C_1$ to $C_3$ alkanoyl e.g. formyloxy or acetoxy, benzyloxy, methanesulfonyloxy, toluene-p-sulfonyloxy, carbamoyloxy, phenylthio, monocyclic heteroaromatic thio containing 3 or more of nitrogen, sulfur and/or oxygen e.g. 1-methyltetrazol-5-ylthio, 1,2,3-triazol-4-ylthio, 1,3,4-thiadiazol-5-ylthio, or 2-methyl-1,3,4-thiadiazol-5-ylthio, tri-$C_1$ to $C_5$-alkyl-silyloxy, bromine, chlorine, and iodine; especially hydroxy, formyloxy, and 1-methyltetrazol-5-ylthio; or X and Y combined together represent an epoxy group;

Z is selected from the group consisting of hydroxy, trimethylsilyloxy, $C_1$ to $C_3$ alkanoyloxy e.g. formyloxy or acetoxy, benzoyloxy, methanesulfonyloxy, toluene-p-sulfonyloxy, phenylselenyl, iodine, bromine, and chlorine; especially, hydroxy, sulfonyloxy, and halo;

COB is selected from the group consisting of carboxy, benzyloxycarbonyl, nitrobenzyloxycarbonyl, methoxybenzyloxycarbonyl, diphenylmethoxycarbonyl, trichloroethoxycarbonyl, t-butoxycarbonyl, sodiooxycarbonyl, and potassiooxycarbonyl.

More specific compounds are given in the Examples.

(Further Modification of the Groups)

When R, COB, X, Y, or Z seems to suffer from unfavorable damages during the reaction, such a sensitive group can be protected in advance and deprotected at an optional and desirable stage after the reaction. Such a desirable treatment is also included in the scope of this invention. For example, carboxy and hydroxy can be protected by conventional methods well known in β-lactam chemistry with, e.g., carboxy-protecting group cited for COB and hydroxy protection as an ester or ether.

II. PROCESS

Compounds I may be prepared from Compounds II by reacting with an addition reagent according to the following scheme in a solvent during the time required for the completion of the reaction at a temperature of about −50° C. to a temperature at which decomposition of starting and produced materials do not take place to an appreciable amount.

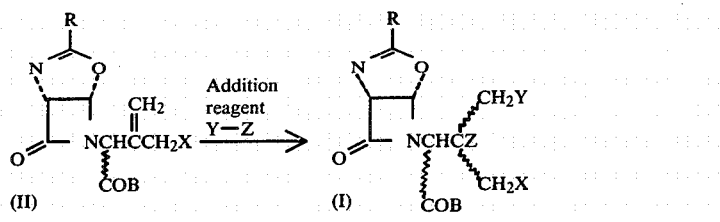

(wherein, R, COB, X, Y and Z are as defined above)

(Addition Reagent)

The addition reagent is one capable of adding to a carbon to carbon double bond including an epoxide-forming reagent (e.g. peracid, selenium dioxide, selenous esters, osmium tetroxide, ruthenium tetroxide, permanganate, lead tetraacetate, thallium trinitrate, potassium chlorate-osmium tetroxide catalyst, hydrogen peroxide, oxygen), hypohalogenous acid-producing reagent (e.g. N-haloamide, N-haloimide, hypohalite ester, chloramine, hypohalite salt), halogenating reagent (e.g. molecular halogen, sulfuryl halide), sulfenyl halide (e.g. phenylsulfenyl halide, nitrophenylsulfenyl halide), oxyhalide (e.g. selenium oxyhalide, chromium oxyhalide), selenyl halide (e.g. phenylselenyl halide), trihaloacetyl halide, and the like reagents represented by Y-Z.

(Solvent)

The solvent can be a hydrocarbon solvent (e.g. hexane, cyclohexane, benzene, toluene), halohydrocarbon solvent (e.g. dichloromethane, chloroform, dichloroethane, trichloroethane, chlorobenzene), ether solvent (e.g. diethyl ether, methyl butyl ether, tetrahydrofuran, dioxane), ketone solvent (e.g. acetone, methyl ethyl ketone, cyclohexanone, benzophenone), ester solvent (e.g. ethyl acetate, isobutyl acetate, methyl benzoate, ethyl benzoate), alcohol solvent (e.g. methanol, ethanol, propanol, isopropanol, t-butanol, benzyl alcohol), and other conventional solvents for organic reactions.

(Reaction Time and Temperature)

The reaction time and temperature depend on the choice of the starting material, reagent, solvent, concentration, and other reaction conditions. Usually, the reaction can be carried out at −50° C. to 100° C., for the reaction with osmium tetroxide, chlorine, or bromine. Generally, the reaction takes about 10 minutes to 50 hours, more preferably from 3 to 20 hours.

(Preferable Example)

In a preferable example, Compound II (1 part) is dissolved in a halohydrocarbon solvent (50 to 200 volumes) and mixed with an addition reagent (1 to 3 equivalents). The mixture is kept at required temperature (−30° C. to 30° C.) for a required time (10 to 200 minutes) for the addition reaction with molecular chlorine.

For the addition reaction with molecular chlorine, irradiation of the reaction mixture with ultraviolet light or visible light may enhance the reaction, although such measure is not required.

(Starting Materials)

6-Epipenicillin 1-oxides derived from 6-epipenicillins are reacted with triphenylphosphine according to the following reaction scheme to yield Compounds (II), the starting materials, and if required, a desirable nucleophilic group may be introduced into the latters.

Chart 1

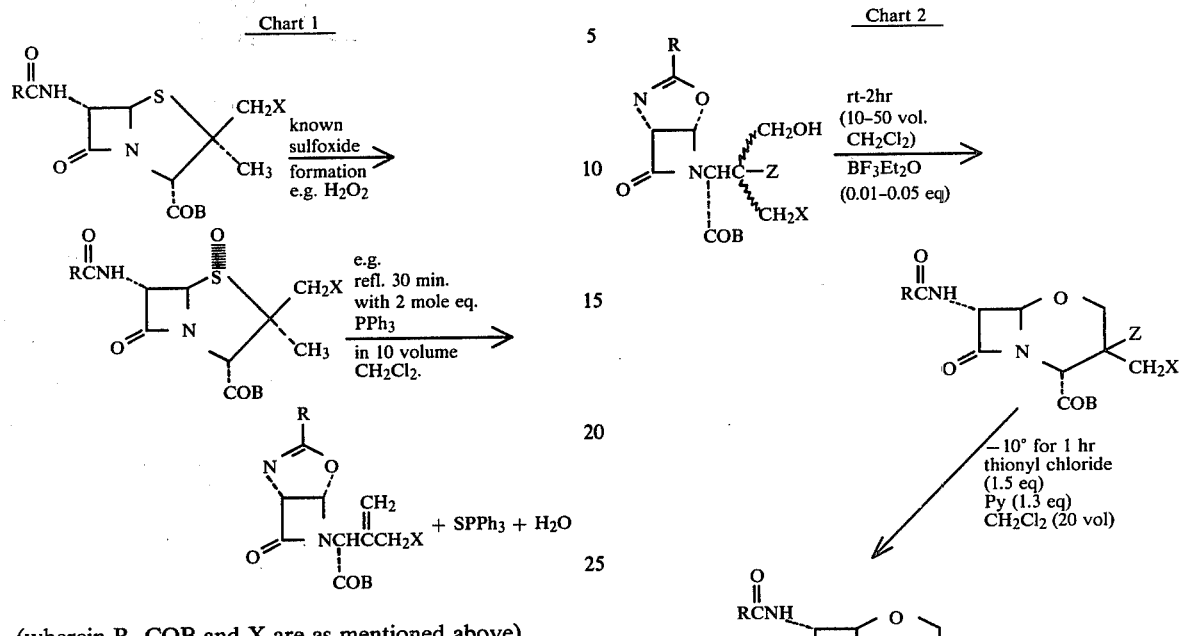

(wherein R, COB and X are as mentioned above)

(Structural Modification of Compounds I)

Those groups R, X, Y, Z, COB are variable from each other within the scope of their definition. For example, (1) Compounds I (X, Y or Z=OH) are reacted with an acylating reagent to yield Compounds I (X, Y or Z=acyloxy).

(2) Compounds I (X or Z=OH) are reacted with a silylating reagent to give Compounds I (X or Z=silyloxy).

(3) Compounds I (X and Z=—O—) are treated with HHal (in which Hal is halogen) to give Compounds I (X=Hal or OH and Z=OH or Hal).

(4) Compounds I (X and Z=—O—) are treated with aqueous acid (e.g. $HClO_4$, $H_2SO_4$) to give Compounds I (X=Z=OH).

(5) Compounds I (X=Hal and Z=OH) are treated with a base to give Compounds I (X and Z=—O—).

(6) Compounds I (X=Hal) are reacted with an acyloxy introducing reagent to give Compounds I (X=acyloxy).

(7) Compounds I (X=Hal) are treated with a hydroxylating reagent (e.g. silver oxide, silver nitrate) to give Compounds I (X=hydroxy).

(8) Compounds I (X=Hal) are treated with an alkylthio introducing reagent, arylthio introducing reagent or heteroaromatic thio introducing reagent to give Compounds I (X=the corresponding thio group).

The compounds thus prepared may be obtained from the reaction mixture by removal of solvent, unreacted starting materials, and by-products by concentration, extraction, washing, or other conventional methods, and then purified by reprecipitation, chromatography, recrystallization or other conventional methods.

III. USE OF COMPOUNDS I

Compounds I may be subjected to cyclization, elimination, inversion and/or other reactions to give valuable 1-oxadethiacephalosporins for example by the route as given in the following Chart 2.

(wherein R, COB, X and Z are the same as mentioned above)

The common nuclei and their numbering of compounds in the examples are shown as follows:

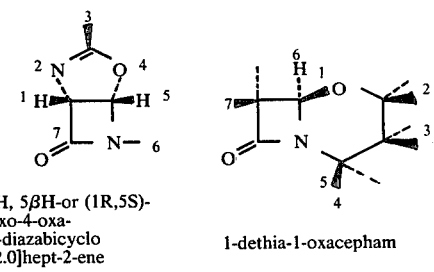

1βH, 5βH- or (1R,5S)-
7-oxo-4-oxa-
2,6-diazabicyclo
[3.2.0]hept-2-ene 1-dethia-1-oxacepham The stereochemical relationship of carbons 1 and 5 in the bicyclohept-2-ene directly corresponds to the configurations of carbons 6 and 5 in 6-epipenicillins or carbons 7 and 6 in oxacephams, respectively.

The stereochemistry around carbon 6 of 1-dethia-1-oxacepham ring system is identical with carbon 6 of cephalosporins at position 6.

Stereochemistry of COB in the formulae is preferably the same as that in penicillins (i.e. R configuration) but not necessarily restricted to it.

In the following Examples, experimental errors in IR-spectra are within ±10 cm$^{-1}$ and those in NMR spectra are within ±0.2 ppm. Melting points are uncorrected. Anhydrous sodium or magnesium sulfate was used for drying every solution.

Physical constants of the products are summarized in Table II.

The following examples are provided to further illustrate this invention. Ph in structural formulae means phenyl.

EXAMPLE 1

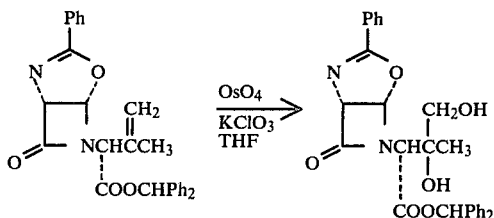

A solution of diphenylmethyl 2-(1R,5S-3-phenyl-7-oxo-4-oxa-2,6-diazabicyclo[3.2.0]hept-2-en-6-yl)-3-methyl-3-butenoate (12.0 g), osmium tetroxide (1 g) and potassium chlorate (12.0 g) in a mixture of tetrahydrofuran (400 ml) and water (200 ml) is stirred at 58° C. for 3.5 hours.

After cooling, the reaction mixture is poured into ice-water and extracted with ethyl acetate. The extract is washed with brine, aqueous 10% sodium thiosulfate and then aqueous sodium hydrogencarbonate, dried over sodium sulfate, and evaporated to yield diphenylmethyl 2-(1R,5S)-3-phenyl-7-oxo-4-oxa-2.6-diazabicylo[3.2.0]hept-2-en-6-yl-3,4-dihydroxy-3-methylbutyrate (12.88 g).

IR: $\nu_{max}^{CHCl_3}$ 3500br, 1770br, 1742, 1636 cm$^{-1}$.

Two stereoisomers may be separated from this product by chromatography on silica gel deactivated with 10% water.

(i) stereoisomer a: NMR: $\delta^{CDCl_3}$ 1.21s3H, 3.52s2H, 4.63s1H, 5.40d(3 Hz)1H, 6.30d(3 Hz)1H, 7.00s1H, 7.1–8.1m15H.

(ii) stereoisomer b: NMR: $\delta^{CDCl_3}$ 1.21s3H, 3.58s2H, 4.57s1H, 5.40d(3 Hz)1H, 6.17d(3 Hz)1H, 7.00s1H, 7.1–8.1m15H.

EXAMPLE 2

In a manner similar to Example 1, Compounds (I) may be prepared from Compounds (II) by reaction with an addition reagent represented by Y-Z in a solvent. The reaction conditions are shown in Table I. The physical constants of the products including those prepared in following examples are shown in Table II.

EXAMPLE 3

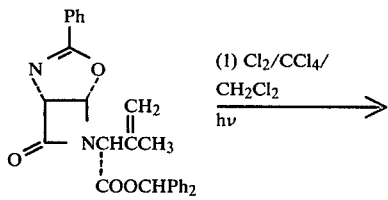

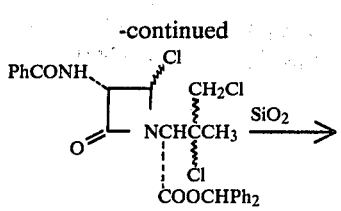

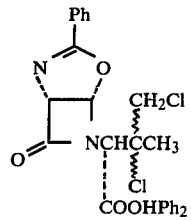

(1) To a solution of diphenylmethyl 2-(1R,5S-3-phenyl-7-oxo-4-oxa-2,6-diazabicyclo[3.2.0]hept-2-en-6-yl)-3-methyl-3-butenoate (200 mg) in dichloromethane (50 ml) is added a 1.66 N solution (0.73 ml) of chlorine in carbon tetrachloride, and the mixture is irradiated with a high pressure mercury lamp (1 KW, through Pyrex filter) for 30 minutes and poured into ice-water. The organic layer is separated, washed with dilute aqueous sodium thiosulfate, cold water, cold aqueous sodium hydrogencarbonate, and then water, dried and evaporated to yield a stereoisomers mixture (253 mg) of diphenylmethyl 2-(3R,4R-3-benzamido-4-chloro-2-oxoazetidin-1-yl)-3,4-dichloro-3-methylbutanoate.

IR: $\nu_{max}^{CHCl_3}$ 3440, 1793, 1744, 1670 cm$^{-1}$.

NMR: $\delta^{CDCl_3}$ 1.93s3H, [4.13s+(4.00d+4.30d)ABq(12 Hz)]2H, 4.4–4.7m1H(4.70s+4.83s)1H, 6.15s1H, (6.93s+7.03s)1H, 7.2–7.8M15H.

(2) The products prepared in above (1) are chromatographed on silica gel deactivated with 10% water. Elution with benzene-ethyl acetate (12:1) yields fractions containing the following products:

(a) one isomer of diphenylmethyl 2-(1R,5S-3-phenyl-7-oxo-4-oxa-2,6-diazabicyclo[3.2.0]hept-2-en-6-yl)-3,4-dichloro-3-methylbutanoate: 35 mg.

IR: $\nu_{max}^{CHCl_3}$ 1789, 1755, 1635 cm$^{-1}$.

NMR: $\delta^{CDCl_3}$ 1.68s3H, 3.57s2H, 4.98s1H, 5.47d(3 Hz)1H, 6.45d (3 Hz)1H, 6.95s1H, 7.2–8.0m15H.

(b) a stereoisomers mixture comprising the above product (a) and the other stereoisomer (c) below: 139 mg.

(c) the stereoisomer of the above product (a): 8 mg.

IR: $\nu_{max}^{CHCl_3}$ 1786, 1754, 1633 cm$^{-1}$.

NMR: $\delta^{CDCl_3}$ 1.78s3H, (3.68d+4.05d)ABq(12 Hz)2H, 5.03s1H, 5.50d(3 Hz)1H, 6.47d(3 Hz)1H, 6.90s1H, 7.2–8.0m15H.

(3) The above reaction (1) may be effected by irradiation with a 300 W-tungsten lamp in place of a high pressure mercury lamp to give the same product.

(4) The above reaction (1) may be effected at −20° C., 0° C., or room temperature without light irradiation to give the same product.

Compounds represented by the following formulae may be also obtained as by-products:

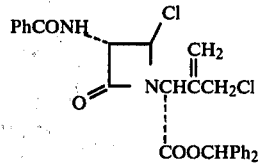

(Compound (1) is found to be convertible into Compound (2) below by thin layer chromatography.)

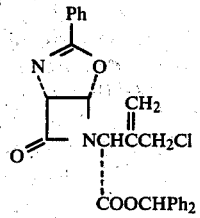

(Compound (2) could be found after silica gel-chromatography. mp. 103°–105° C.), and

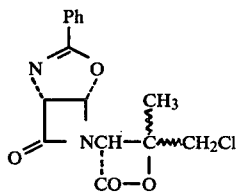

(Compound (3) could be found after silicagel-chromatography. mp. 167°–170° C.).

(5) The reaction (1) may be carried out by employing t-butyl hypochlorite (60 μl) in a mixture of chloroform (10 ml) and carbon tetrachloride (40 ml) in place of chlorine in methylene chloride-carbon tetrachloride of the reaction described above (1), and succeeding irradiation with a high pressure mercury lamp (1 KW/through pyrex filter) for 2.5 hours to give the same product.

Modification 1—(O-Acylation)

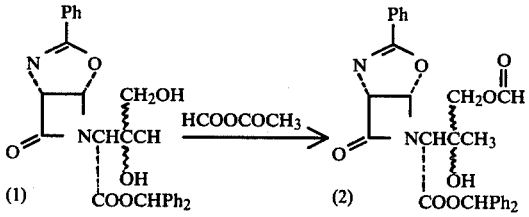

To a solution of Compounds (1) prepared in Example 1 (3.18 g) in dichloromethane (35 ml) are added 6 ml of pyridine (6 ml) and formic acetic mixed anhydride [prepared by reacting formic acid (1.9 ml) and acetic anhydride (4.8 ml) at 0° C. for 30 minutes], and the mixture is allowed to stand at 0° C. overnight, poured into ice-water and extracted with dichloro methane. The extract is washed with dilute hydrochloric acid, aqueous sodium hydrogencarbonate and then water, dried, and evaporated. The residue (3.2 g) is chromatographed on silica gel (50 g) to yield the monoformate Compound (2) (2.66 g). This product is a mixture of stereoisomers at the 3-substituent.

Modification 2—(Epoxide cleavage)

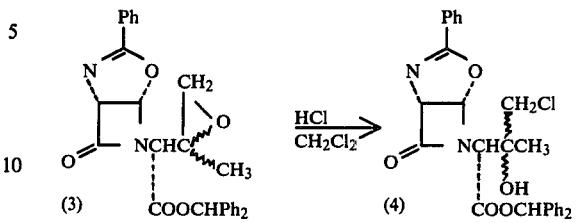

To a solution of Compounds (3) (150 mg) in dichloromethane (5 ml) is added concentrated hydrochloric acid (0.2 ml) under ice-cooling, and the mixture is stirred for 40 minutes and then mixed with aqueous 5% sodium hydrogencarbonate. The organic layer is separated, washed with water and brine, dried, and evaporated. The residue is chromatographed on silica gel (9 g). Elution with benzene ethyl acetate (5:1) yields diphenylmethyl 2-(1R,5S-3-phenyl-7-oxo-4-oxa-2,6-diazabicyclo[3.2.0]hept-2-en-6-yl)-4-chloro-3-hydroxy-3-methylbutyrate (4) in 74% yield as a mixture (120 mg) of stereoisomers at the 3 position.

Modification 3—(O-Silyation)

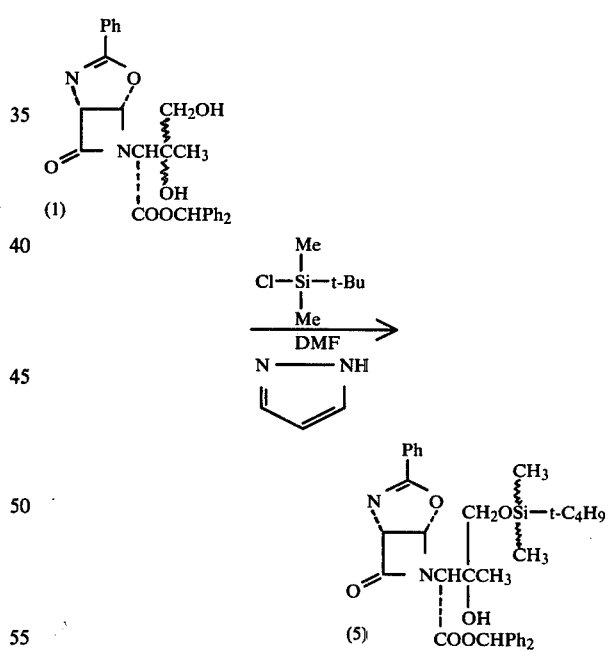

To a solution of imidazole (0.68 g) and t-butyldimethylsilyl chloride (1.5 g) in N,N-dimethylformamide (10 ml) is added Compound (1) prepared in Example 1 (3.41 g), and the mixture is kept at room temperature for 16 hours, poured into ice-water, and extracted with ethyl acetate. The extract is washed with saturated aqueous sodium chloride, dried over magnesium sulfate, and evaporated to yield the corresponding mono t-butyldimethylsilyl ether (5) (3.66 g=87% yield) as a mixture of stereoisomers of the 3-substituent.

Modification 4—(O-silylation 2)

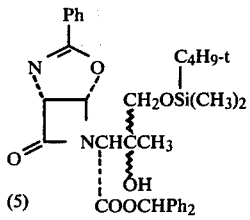
(5)

rt 24 hrs.
BSA
Me₃SiCl
⟶
Py

-continued

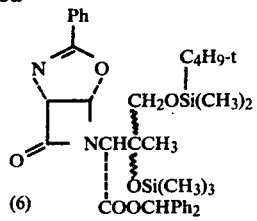
(6)

To a solution of the product (300 mg) of the preceding Modification 3 in pyridine (2 ml) are added bistrimethylsilylacetamide (508 mg) and trimethylsilyl chloride (108 mg), and the reaction mixture is stirred at room temperature for 24 hours and then evaporated in vacuo. The residue is diluted with 10 ml of saturated aqueous sodium chloride and extracted with ethyl acetate. The extract is washed with saturated aqueous sodium chloride, dried over magnesium sulfate, and evaporated to yield Compounds (6) (327 mg=97% yield) as a mixture of stereoisomers of the 3-substituent.

Table I $$\underset{(II)}{\begin{array}{c}R\\\diagdown\\\text{oxazoline-}\beta\text{-lactam with }CH_2=CCH_2X,\ NCHCOOR^1\end{array}} \xrightarrow{Y-Z} \underset{(I)}{\begin{array}{c}R\\\diagdown\\\text{oxazoline-}\beta\text{-lactam with }CH_2Y,\ NCHCH(Z)CH_2X,\ COOR^1\end{array}}$$

| NO. | R— | —R¹ | —X | —Y | —Z | Starting material II (g) | Solvent (ml) | Reagent (g) | Temp. (°C.) | Time (hour) | Yield I (g) | Yield I (%) |
|---|---|---|---|---|---|---|---|---|---|---|---|---|
| 1 | Ph— | —CHPh₂ | —H | —OH | —OH | 1.0 | THF(200) H₂O(100) | OsO₄(0.45) KClO₃(5.0) | 50-60 | 5 | 5.23 | isomers mixture |
| 2 | " | " | —Cl | " | " | 12.0 | THF(11) H₂O(5) | OsO₄(0.05) KClO₃(0.5) | 50 | 8 | (a)0.358 (b)0.642 | 93 |
| 3 | " | " | -S-C(=N-N(CH₃)-N=) (methyltetrazolylthio) | " | " | 0.206 | THF(7.46) H₂O(3.5) | OsO₄(0.046) KClO₃(0.2) | 55 | 3.5 | 188 | — |
| 4 | " | " | —Br | " | " | 0.230 | THF(6) H₂O(2) | OsO₄(0.1) KClO₃(0.2) | rt | 15 | (a)53 (b)88 (a+b)96 | 97 |
| 5 | " | " | —H | —O— | | 9.45 | CHCl₃(250) | m-CPBA(8.44) NaHCO₃(8.82) | rt | 48 | 4.81 | — |
| 6 | " | " | " | —Cl | —SePh | 0.30 | CH₂Cl₂(2) | PhSeCl/CH₂Cl₂ (0.127) | rt | 8 | 0.248 | — |
| 7 | " | " | " | —OH or —Br | —Br or —OH | 0.50 | CH₃COCH₃(12) H₂O(1.2) | NBS(0.3) | 0 + rt | 0.7 + 1.5 | (a)0.159 (b)0.255 | 26 42 |

(Abbreviation)
CPBA = chloroperbenzoic acid,
NBS = N-bromosuccinimide,
Ph = phenyl,
rt = room temperature,
THF = tetrahydrofuran
(a), (b) = a pair of stereoisomers at the 3 position Table II

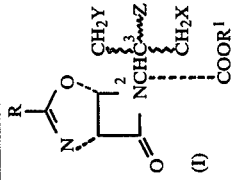

(I)

| No. | R— | $R^1$ | —X | —Y | —Z | mp. (°C.) | IR:$\nu_{max}^{CHCl_3}$ cm$^{-1}$ | NMR:$\delta^{CDCl_3}$ (Hz value represents coupling constant) |
|---|---|---|---|---|---|---|---|---|
| 1. | Ph— | —CHPh$_2$ | —H | —OH | —OH | — | 3500br, 1770br, 1742, 1636. | 1.20 or 1.22s3H, 3.52s2H, 4.63s1H, 5.40d(3Hz)1H, 6.30d(3Hz)1H, 7.00s1H, 7.1–8.1m15H. |
| 2. | " | " | " | " | " | — | " | 1.20 or 1.22s3H, 3.58s2H, 4.57s1H, 5.40d(3Hz)1H, 6.17d(3Hz)1H, 7.00s1H, 7.1–8.1m15H. |
| (Compounds of No. 1 and No. 2 are stereoisomers at the 3 position) |
| 3. | " | " | —Cl | " | " | — | 3600–3150br, 1780–1735br. | 2.6–3.2br1H, (3.42d+3.78d)ABq(11Hz)2H, 3.83brs2H, 4.72s1H, 5.37d(3Hz)1H, 5.97d(3Hz)1H, 6.98s1H, 7.2–7.6m13H, 7.8–8.0m2H. |
| 4. | " | " | " | " | " | — | 3600–3100br, 1785–1740br. | 2.6–3.0br1H, 3.68s4H, 4.2–4.5br1H, 4.80s1H, 5.42d(3Hz)1H, 618d(3Hz)1H, 6.93s1H, 7.2–7.6m13H, 7.8–8.0m2H. |
| (Compounds of No. 3 and No. 4 are stereoisomers at the 3 position) |
| 5. | " | " | ![triazole-S] | " | " | — | 3380br, 1768br, 1634. | (Stereoisomer at the 3 position) Rf 0.17 Silica gel plate (Merck) 0.20 benzene + ethyl acetate (1:1) |
| 6. | " | " | —H | —OCHO | " | — | 3520, 3400, 1778, 1731, 1633, 1603, 1580. | 1.25+1.30s3H, [4.07s+4.13s+4.30s+4.36s]2H, (4.46s+4.50s)1H, 5.03–5.04m1H, 6.05–6.15m1H, 6.90s1H, 7.13–7.3m13H, 7.8–8.0m3H. |
| (A mixture of stereoisomers at the 3 position) |
| 7. | " | " | —Br | —OH | " | — | 3600–3150br, 1785–1740br. | 2.03–2.56br2H, 3.30+3.67ABq(11Hz)2H, 3.83brs2H, 4.75s1H, 5.35d(3Hz)1H, 5.90d(3Hz)1H, 6.98s1H, 7.27–7.57m13H, 7.87–8.10m2H. |
| 8. | " | " | " | " | " | — | 3600–3200br, 1785–1740br. | 2.83–3.17br2H, 3.55s2H, 3.72s2H, 4.85s1H, 5.42d(4Hz)1H, 6.20d(4Hz)1H, 6.92s1H, 7.13–7.53m13H, 7.77–8.00m2H. |
| (Compounds of No. 7 and No. 8 are stereoisomers at the 3 position) |
| 9. | " | " | —H | —Cl | " | — | 1785, 1765, 1743, 1633, 1602, 1175, | (1.32s+1.42s)3H, 3.3–3.8m2H, (4.60s+4.67s)1H, [5.32d(3.5Hz)+5.37d(3.5Hz)]1H, [5.90d(3.5Hz)+6.07d(3.5Hz)]1H, (6.95s+6.87s)1H, (7.3–7.5m+7.8–8.0m)15H. |
| (A mixture of stereoisomers at the 3 position) |

Table II-continued

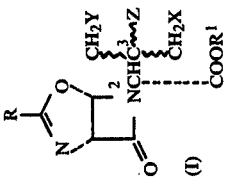

(I)

| No. | R— | —R[1] | —X | —Y | —Z | mp. (°C.) | IR:$\upsilon_{max}^{CHCl_3}$ cm$^{-1}$ | NMR:$\delta^{CDCl_3}$ (Hz value represents coupling constant) |
|---|---|---|---|---|---|---|---|---|
| 10. | " | " | " | " | —SePh | — | 1788, 1755, 1633, 1603. | 1.68s3H, 3.5brs2H, 5.17s1H, 6.48d(3.5Hz)1H, 5.45d(3.5Hz)1H, 6.92s1H, (7.3–7.5m+7.8–8.1m) 15H. |
| 11. | " | " | " | —O— | | 157–161 | 3000, 1788, 1750, 1633, 1602. | (1.33s+1.37s)3H, 2.6–3.0m2H, (4.23s+4.37s)1H, 5.38d(4Hz)1H, [6.18d(4Hz)+6.22d(4Hz)]1H, (6.93s+6.97s)1H, (7.3–7.5m+7.8–8.1m)15H |

(A mixture of stereoisomers at the 3 position)

| 12. | " | " | " | —O—Si—CH$_3$ CH$_3$ t-C$_4$H$_9$ | —OH | — | 1630, 1735, 1773, 1780. | —0.01s3H, —0.02s3H, 0.77s9H, 1.23s3H, 3.42s 2H, (3.50s+4.03s)1H, 4.53s1H, [5.18d(2.5Hz)+ 5.23d(2.5Hz)]1H, [5.96d(2.5Hz)+6.02d(2.5Hz)] 1H, (6.66s+6.72s)1H, (6.8–7.3m+7.5–7.77m)15H |

(A mixture of stereoisomers at the 3 position)

| 13. | " | " | " | —OH | —Br | 159–160 | 3200, 1788, 1733. | 1.70s3H, 3.79brs3H, 4.9s1H, 5.47d(3Hz)1H, 6.63d1H, 7.03s1H, 7.2–8.0m15H. |
| 14. | " | " | " | —Br | —OH | — | 3370, 1780, 1743sh, 1634. | (1.37s+1.46s)3H, [3.33s+(3.40+3.43)ABq]2H, (4.66s+4.77s)1H, [5.38d(3Hz)+5.44d(3Hz)]1H, [5.9d(3Hz)+6.15d(3Hz)]1H, (6.88s+6.98s)1H, 7.2–8.2m15H. |

(Compounds of No. 13 and No. 14 are stereoisomers at the 3 position)

| 15. | " | " | " | —O—Si—OH CH$_3$ t-C$_4$H$_9$ | —OSi(CH$_3$)$_3$ | — | 1780, 1755, 1630. | (−0.08s+ −0.04s+0.04s+0.08s+0.19s)15H, (0.83s+0.89s)9H, (1.27s+1.33s)3H, 3.27–3.83m 2H, (4.58s+4.65s)1H, [5.30d(2.5Hz)+5.35d (2.5Hz)]1H, [6.27d(2.5Hz)+6.33d(2.5Hz)]1H, 6.8s1H, (7.0–7.07m+7.57–7.87m)15H. |

(A mixture of stereoisomers at the 3 position)

What we claim is:
1. A compound of the formula
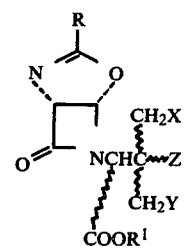
wherein R is phenyl, R¹ is diphenylmethyl, X is hydrogen, chlorine, bromine, or 1-methyl-tetrazolylthio, Y is hydroxy, formyloxy, t-butyldimethylsilyloxy, chlorine or bromine, and Z is hydroxy, phenylselenyl, trimethylsilyloxy, chlorine or bromine.
* * * * *